United States Patent
Giveen

[11] Patent Number: 5,860,387
[45] Date of Patent: Jan. 19, 1999

[54] AUTOMATIC SQUEEZE-BOTTLE UTILIZATION CYCLE COUNTING DEVICE

[76] Inventor: Samuel Charles Giveen, 1220 Chestnut St., Apt. A, Alameda, Calif. 94501

[21] Appl. No.: 866,896

[22] Filed: May 30, 1997

[51] Int. Cl.⁶ .............. B67D 5/12; G01D 13/00; G09F 11/00
[52] U.S. Cl. ............ 116/285; 206/227; 206/459.1; 215/230; 222/27; 222/32; 116/315
[58] Field of Search ................ 116/285, 298, 116/308, 309, 311, 312, 315, 223, 284; 206/459.1, 277; 215/230, 203, DIG. 3; 235/66, 85 R; 222/27, 32, 44, 38

[56] References Cited

U.S. PATENT DOCUMENTS

| | | | |
|---|---|---|---|
| 2,636,469 | 4/1953 | McKay | 116/312 |
| 3,735,099 | 5/1973 | Herr | 235/91 R |
| 4,037,719 | 7/1977 | Perlmutter | 206/266 |
| 4,207,982 | 6/1980 | Maxwell et al. | |
| 4,528,933 | 7/1985 | Allen | |
| 4,548,157 | 10/1985 | Hevoyan | |
| 4,565,302 | 1/1986 | Pfeiffer et al. | 222/38 |
| 4,634,012 | 1/1987 | Kelley | |
| 4,817,822 | 4/1989 | Rand et al. | 222/38 |
| 5,174,473 | 12/1992 | Marelli | 22/38 |
| 5,280,834 | 1/1994 | Berkeley | |
| 5,356,012 | 10/1994 | Tang et al. | |

Primary Examiner—Elizabeth L. Dougherty
Assistant Examiner—Willie Morris Worth

[57] ABSTRACT

An automatic squeeze-bottle utilization cycle counting device in the form of a squeeze bottle, a bottle cap having a nozzle attached to the squeeze bottle and a removable nozzle cap hinged to the bottle cap for isolating the nozzle from the outside environment. An indicating mechanism indicates the number of times the nozzle cap has been removed and replaced is provided in the form of a rotatable part rotatably attached to the bottle cap, a set of symbols on the rotatable part, a window in the nozzle cap for sequential indication of the symbols and cooperating ratchet elements on the rotatable part and the nozzle cap for indexing the rotatable part. The device provides positive positioning of the nozzle cap and allows tracking of compliance with a prescribed regimen which includes using the contents of the squeeze-bottle, while decreasing the risk of contamination of the nozzle and the contents of the bottle.

1 Claim, 4 Drawing Sheets

AUTOMATIC SQUEEZE-BOTTLE UTILIZATION CYCLE COUNTING DEVICE

BACKGROUND

1. Field of Invention

The present invention relates to liquid containment and dispensing devices which are hand held and resealable, as well as to devices which incorporate use-cycle counting mechanisms.

2. Discussion of Prior Art

The uses of liquid pharmaceutical agent dispensing bottles:

Many liquid pharmaceutical agents prescribed for repeated therapeutic use and solutions used for the maintenance of eye contact lenses are distributed in plastic squeeze-bottles. These agents typically are dispensed by the user through an orifice which is covered by a screw-on or snap-on cap when not in use.

The necessity of keeping track of use cycles with liquid pharmaceutical and eye contact lens liquid agents:

End users of eye contact lens solutions and therapeutic eye drops are faced with the necessity of keeping track of the number of dispensings performed in a given period of time, or the total number of executions of an associated activity. For example, therapeutic eye drops may be prescribed for use four times per day. As a second example, disposable soft eye contact lenses are often prescribed for 14 days of wear with nightly removal, cleaning and storage prior to disposal. Wearers must keep track of the total number of days during which a particular pair of such lenses has been worn. These counts are often important to the management of existing diseases and to the prevention of new disease states. Keeping count mentally is a method offering poor accuracy.

Devices which allow use cycle tracking for pharmaceutical agents:

A number of mechanical devices are known which allow patients to keep track of their utilization of pills. U.S. Pat. Nos. 4,528,933 to Allen, July, 1985, 4,634,012 to Kelley, January, 1987 and 5,356,012 to Tang and Yang, October, 1994 describe pill bottles with fully removable caps in which automatic indexing devices are incorporated for the purpose of tracking dispensing cycles. These cannot be used for dispensing liquids in a controlled fashion.

U.S. Pat. No. 2,636,469 to McKay, January, 1952, describes a capsule dispenser which indicates the fact that the container has been opened and a capsule has been removed during sequential time periods. McKay's device differs from the current invention in that it has a cap which slides linearly and is held captive on the container. It has neither facility for sealing, nor a nozzle nor a hinged nozzle cap and cannot be used for dispensing liquids in a controlled fashion.

U.S. Pat. No. 4,817,822 to Rand et al, April, 1989, describes a use cycle counting device attached to an aerosol bottle such as those used for dispensing inhalable atomized medications. The device of Rand et al differs from the current invention in that it uses a pressurized aerosol cannister rather than a manually deformable squeeze bottle. Indexing is by linear compression of the nozzle toward the bottle, rather than detachment of a hinged nozzle cap in an arcuate manner. The device of Rand et al has neither a hinge nor an attached nozzle cap for the isolation of the nozzle.

U.S. Pat. No. 3,735,099 to Herr, May, 1973, describes a use cycle counting cigarette lighter wherein opening and closing the cover serves to index a ratchet wheel. Herr's device differs from the current invention in that it includes a rigid case rather than a manually deformable squeeze bottle, an aperture containing a wick rather than a nozzle and means for striking a spark.

U.S. Pat. Nos. 4,565,302 to Pfeiffer et al, January, 1986 and 5,174,473 to Marelli, December, 1992, describe use cycle counting devices attached to bottles of the type used for dispensing nasal spray. These devices differ from the current invention in that they include piston pumps for expelling liquid contents rather than relying upon the generation of pressure by squeezing a manually deformable bottle. Indexing is by linear compression of the a collar toward the bottle, rather than detachment of a hinged nozzle cap in an arcuate manner. The device of Pfeiffer et al and the device of Marelli have neither hinges, nor attached nozzle caps, nor indexing means attached to the nozzle caps for the isolation of the nozzles.

U.S. Pat. No. 4,207,982 to Maxwell and Crisp, June, 1980, describes a pill bottle with an automatically indexing flip-top closure which remains attached to the bottle. It does not provide facility for incorporation of a fluid-tight seal and, likewise, cannot be used for dispensing liquids in a controlled fashion.

The patient's memory is generally relied upon as assurance of proper dosing and dispensing of medications and use of eye contact lens solutions. Calendars and paper records are often recommended, but their utility is limited by the user's diligence and ability in keeping the records up-to-date. A contact lens storage case is known which provides a manually operated wheel, bearing a sequence of numerals to keep a running total of days of use, shown in U.S. Pat. No. 5,280,834 to Berkley, January, 1994. Effective use of this device depends upon the patient's diligence and ability in indexing the wheel exactly once for each daily cycle as the device does not provide for automatic operation.

A device with a manually rotatable element has been applied to a liquid dispenser as shown in U.S. Pat. No. 4,548,157 to Hevoyan, October, 1985. This device similarly depends upon manual operation and user diligence and ability in proper indexing, having no facility for automatic operation.

Discussion of Problems Addressed by the Invention

The difficulty encountered by sporadic contact lens users in tracking use cycles:

In addition to tracking the use of disposable contact lenses worn on a waking-hours-only basis, generally used with a recommended fourteen-day replacement cycle, counts of days of use must be kept in the performance of periodic enzymatic contact lens cleanings, most often recommended on a seven day of wear cycle. These schedules are less difficult to keep when lenses are used consistently on consecutive days. Patients who use their lenses less frequently than every day, however, often have only a vague idea of how many uses a particular pair of contact lenses has undergone. Since less frequent contact lens disposal presents a lower immediate financial cost to the patient, these patients tend to err in the direction of wearing their lenses for more days than prescribed, or of enzymatically cleaning their lenses less frequently than prescribed. As this can negatively affect the patient's eye health as well as decreasing the volume of materials sold, compliance with such regimens is a cause of much concern in the eye care and contact lens industry.

Regimen noncompliance by patients using therapeutic eye drops:

While necessary for disease management, therapeutic eye drops such as those used in glaucoma therapy, are often irksome to patients, expensive to purchase and may induce undesirable physiological side effects. Many patients' compliance with eye drop instillation frequency instructions is compromised by waning motivation, failing memory and lack of adequate attention. Perhaps the best example is patients under topical medical therapy for glaucoma, generally a disease of the elderly. These patients very frequently comply incompletely with their prescribed regimens of, generally, one to four eye drop instillations per day for life. Such noncompliance is typically unintentional and contributed to by the negative influences previously mentioned. When the patient is under an appropriate regimen, the result of such noncompliance may be a chronic elevation of fluid pressure within the eye and otherwise avoidable permanent loss of visual function.

The inadvertent contamination easily allowed by commonly used cap designs:

Hinged bottle caps are well known in the prior art, but are not commonly used in packaging the aforementioned eye contact lens solutions and topical liquid medical eye drops Currently used snap-on nozzle caps which are tethered to main bottle caps, such as those commonly used on eye contact lens maintenance solutions, are designed in such a way as to make the avoidance of digital contamination of the nozzle, during manual removal and replacement of the nozzle cap, extremely difficult. This configuration also allows contact between the lower edge the nozzle cap, which is often touched with the fingers during removal, and the nozzle, due to indefinite relative positioning of the nozzle and the nozzle cap. A screw-on nozzle cap is frequently set down upright on an unsanitary surface and, subsequently, its lower surface is easily touched to the nozzle during removal and replacement, allowing contamination of the nozzle and the contents. In addition, in part due to their small size, snap-on nozzle caps can be quite difficult to remove, sometimes resulting in them being left off entirely or removed with the user's teeth, either of which actions degrades hygiene, thereby increasing the risk of ocular infection.

SUMMARY DESCRIPTION OF THE INVENTION

The present invention is a device, to be either attached to, or included as part of, a liquid containment and dispensing apparatus, such as those used with eye contact lens maintenance solutions and therapeutic medical eye drops, which are stored and distributed in manually deformable bottles. This invention furnishes the containment and dispensing functions of the commonly used apparatuses. In addition, by means of a hinge, it provides positive relative location of the nozzle and the nozzle cap, thereby decreasing the risk of contamination of the contents. Finally, by use of a mechanical rotary indexing mechanism which bears icons, it provides information to the user regarding the number of times the apparatus has been used during a given cycle, to assist the user in complying with a prescribed regimen.

In particular, in a first embodiment, the invention is a resealable container apparatus for the containment and dispensing of liquid contents thereof, and for the automatic recording of the number of serial dispensings performed or yet to be performed in a given cycle, comprising, a deformable bottle, an orifice member, for permitting the expulsion of said liquid contents, securing means, for securing said orifice member to said bottle, removably attachable sealing means, allowing the isolation of said orifice member and the remaining portion of said liquid contents from the outside environment, and alternately, allowing the expulsion of said liquid contents, a hinge apparatus, connecting said sealing means to an item selected from the group consisting of said bottle, said securing means and said orifice member, a rotatable part, indexing means comprising a plurality of serial indexing surfaces and a drive pawl, providing automatic, unidirectional, rotational indexing of said rotatable part, during each cycle of removal of said sealing means from and reattachment of said sealing means to an item selected from the group consisting of said orifice member, said securing means and said bottle, reverse rotation prevention means, for preventing reverse rotation of said rotatable part, a set of symbols, comprising symbols, one or more in number, and indicating means, for the sequential indication of said symbols of said set of symbols, whereby one can be assisted in maintaining and monitoring compliance with a prescribed regimen which includes using the contents of said bottle at a certain frequency in time or relative to some associated activity, and decreasing the risk of contamination of said orifice member and of said contents by providing positive positioning of said sealing means relative to said orifice member.

As a variation on this first embodiment, said bottle bears a liquid discharge member and a first screw thread, as do those commonly employed for containment and dispensing of therapeutic medical eye drops, said apparatus exclusive of said bottle bears a second screw thread, complimentary to said first screw thread, and said apparatus exclusive of said bottle bears liquid discharge member sealing means for sealing said apparatus exclusive of said bottle against said liquid discharge member upon the engagement of said first screw thread with said second screw thread. Said hinge apparatus comprises angular situating means, for influencing said sealing means to remain in a certain position when sealing means has been removed from orifice member.

A second embodiment of the invention is an automatic use cycle counting apparatus for attachment to and use in conjunction with a liquid containment and dispensing apparatus, said liquid containment and dispensing apparatus comprising a deformable bottle, a liquid discharge member and a liquid discharge member cap, such as an apparatus of the type commonly employed for eye contact lens maintenance solutions, said exemplary liquid containment and dispensing apparatus comprising a deformable squeeze bottle, a bottle cap bearing an integral liquid discharge member, and a tethered liquid discharge member cap, said counting apparatus and said liquid containment and dispensing apparatus, when used in conjunction, being for the containment and dispensing of liquid contents thereof and for the automatic recording of the number of serial dispensings performed, or yet to be performed, in a given cycle, said use-cycle counting apparatus comprising, base attachment means for attachment of said counting apparatus to said liquid containment and dispensing apparatus exclusive of said liquid discharge member cap, liquid discharge member cap attachment means for attachment of said counting apparatus to said liquid discharge member cap, a hinge apparatus, connecting said base attachment means with said liquid discharge member cap attachment means, providing positive positioning of said liquid discharge member cap relative to said liquid discharge member during removal of said liquid discharge member cap from and replacement of said liquid discharge member cap on said liquid discharge member, a rotatable part, indexing means, comprising a plurality of serial indexing surfaces and a drive pawl, for automatic, rotational indexing of said rotatable part, during each cycle of removal of said liquid discharge member cap from and reattachment of said liquid discharge member cap to said liquid discharge member, reverse rotation prevention means, for preventing reverse rotation of said rotatable part, a set of symbols, comprising symbols, one or more in number, and indicating means, for the sequential indication of said symbols of said set of symbols, whereby one can be assisted in maintaining and monitoring compliance with a prescribed regimen which includes using the contents of said bottle at a certain frequency, in time or relative to an associated activity, while decreasing the risk of contamination of said orifice member and of said contents by providing positive positioning of said sealing means relative to said orifice member.

OBJECTS AND ADVANTAGES

Accordingly several objects and advantages of the present invention are:

to provide a resealable containment and counting apparatus which provides sanitary enclosure of liquid contents, provides facility for dispensing these contents in a controlled fashion and automatically informs the user of the number of times the apparatus has been, or has yet to be, either opened or closed or both, as a running total or relative to a given time period, or by association, the number of times another related activity has been performed, to reduce the user's dependence upon memory in complying with medical therapeutic regimens which utilize liquid pharmaceutical agents and in complying with eye contact lens maintenance regimens, thereby improving the accuracy of compliance with prescribed regimens, to simplify and make more convenient the task of keeping track of the number of times the containment apparatus has been either opened or closed or both, as a running total or relative to a given time period, or by association, the number of times another related activity has been performed.

to facilitate manual removal and replacement of the nozzle closure, and to decrease the risk of contamination of the nozzle, thereby decreasing the risk of contamination of the contents of the bottle and of the expelled liquid, with a resultant decrease in the risk of ocular infection.

Further objects and advantages of the present invention will become apparent from a consideration of the drawings and ensuing descriptions.

DRAWING FIGURES

Figure 1A:
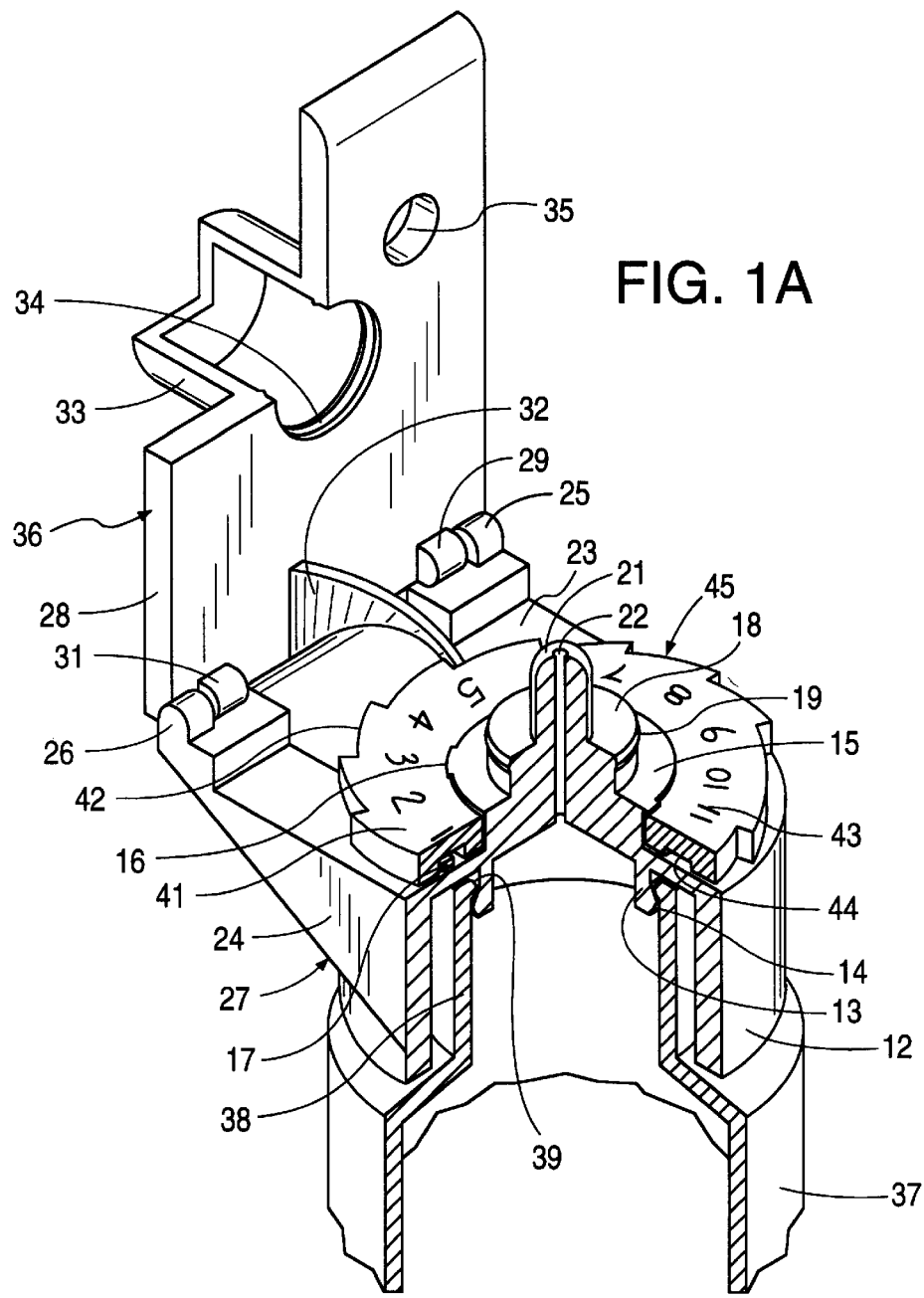
FIG. 1A depicts the preferred embodiment of the present invention, in which the counting mechanism is integrated into a full cap, nozzle, nozzle cap and bottle assembly, assembled, in the open condition, in perspective view, sectioned to illustrate detail.

Reference Numerals Used in the Drawings
Features of the Preferred Embodiment
bottle cap 12
insertion ring 13
insertion ring lip 14
bearing boss 15
set of retention lips 16
backcheck pawl 17
sealing boss 18
sealing boss lip 19
nozzle 21
through hole 22
right support 23
left support 24
right lower hinge barrel 25
left lower hinge barrel 26
sealing cap 27
cover 28
right upper hinge barrel 29
left upper hinge barrel 31
worm gear sector 32
nozzle cap 33
nozzle cap lip 34
window 35
cap cover 36
bottle 37
bottle neck 38
bottle neck lip 39
ring 41
radial ratchet tooth set 42
symbol set 43
axial ratchet tooth set 44
indicator ring 45
Features of the First Alternate Embodiment
threaded tube 46
base plate 47
sealing protuberance 48
sealing protuberance edge 49
reversal prevention pawl 51
drive pawl 52
spout 53
sealing cavity 54
communicating hole 55
living hinge 56
cover plate 57
spout cap 58
spout cap edge 59
bearing protuberance 61
set of keeper lips 62
character set 63
sealing top 64
vessel body 65
vessel neck 66
vessel nozzle 67
transmission hole 68
vessel 69
wheel 71
outer ratchet tooth set 72
lower ratchet tooth set 73
indicator arrow 74
indicator wheel 75
Features of the Second Alternate Embodiment
lower gripping plate 76
support wall 77
left lower leg 78
lower slot 79
left integral hinge 81
right integral hinge 82
left upper leg 83
right upper leg 84 upper gripping plate 85
upper slot 86
side-mounted journal 87
set of holding lips 88
thrust pawl 89
pointer arrow 91
antireversion pawl 92
gripping unit 93
disc 94
first ratchet tooth set 95
first numeral set 96
second ratchet tooth set 97
second numeral set 98
indicator disc 99

DESCRIPTION OF THE PREFERRED EMBODIMENT

Figure 1B:
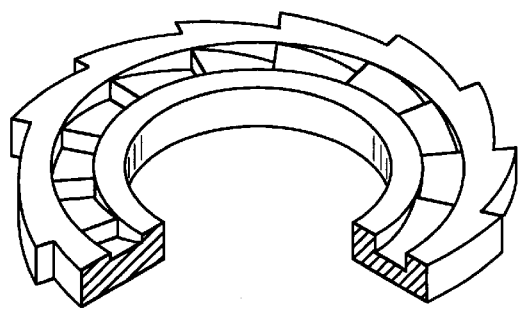
FIG. 1B depicts the underside of the ring of the preferred embodiment of the invention shown in FIG. 1A, sectioned to illustrate detail.

FIGS. 1A and 1B

FIG. 1A is an assembly view with break-away sections illustrating the preferred embodiment of the invention. A cylindrical bottle cap 12 comprises an inner cylindrical surface centered about an axis, an outer cylindrical surface centered about this axis and a flat circular plate at its upper end, perpendicular to this axis, bottle cap 12 being open at its lower end. A hollow cylindrical insertion ring 13, comprising an inner cylindrical surface and an outer cylindrical surface, both centered about the axis of bottle cap 12, projects downward from plate of bottle cap 12. A raised insertion ring lip 14 extends radially outward from outer surface of insertion ring 13. A bearing boss 15 comprising an outer cylindrical surface centered about the axis of bottle cap 12 and a flat upper surface, perpendicular to this axis, projects upward from the plate of bottle cap 12. A set of retention lips 16, equally spaced, three in number, protrudes radially outward from the outer surface of bearing boss 15, adjacent to the upper surface of bearing boss 15. A wedge-shaped backcheck pawl 17 projects upward from the plate of bottle cap 12 between the outer surface of bottle cap 12 and the outer surface of bearing boss 15, sloping upward in the direction of counter-clockwise rotation about the axis of bottle cap 12. A cylindrical sealing boss 18, comprising an outer cylindrical surface centered about the axis of bottle cap 12, and a flat upper surface, perpendicular to this axis, projects upward from the upper surface of bearing boss 15. A raised sealing boss lip 19 protrudes radially outward from the outer surface of sealing boss 18 adjacent to the upper surface of sealing boss 18. A cylindrical nozzle 21, centered about the axis of bottle cap 12, projects upward from the upper surface of sealing boss 13. A through hole 22, centered about the axis of bottle cap 12, connects the cavity within bottle cap 12 with the space above nozzle 21. A right support 23, comprising an upper surface and a rear surface, extends backward from the outer surface of bottle cap 12 and extends upward to the plane which includes the upper surface of bearing boss 15. A left support 24, comprising an upper surface and a rear surface, extends backward from the outer surface of bottle cap 12 and extends upward to the plane which includes the upper surface of bearing boss 15. A right lower hinge barrel 25, comprising a concave spherical left surface, extends upward from the upper surface of right support 23 adjacent to the rear surface of right support 23. A left lower hinge barrel 26, comprising a concave spherical right surface, extends upward from the upper surface of left support 24 adjacent to the rear surface of left support 24. Sealing cap 27 is a single part molded of firm, flexible plastic material and comprises bottle cap 12, insertion ring 13, insertion ring lip 14, bearing boss 15, set of retention lips 16, backcheck pawl 17, sealing boss 18, sealing boss lip 19, nozzle 21, through hole 22, right support 23, left support 24, right lower hinge barrel 25 and left lower hinge barrel 26.

A flat rectangular cover 28, comprising an upper surface, a lower surface, a rear surface and a cylindrical hole, centered about the axis of bottle cap 12, lies parallel to and in close juxtaposition to the upper surface of bearing boss 15. A right upper hinge barrel 29, comprising a convex spherical right surface, extends downward from the lower surface of rectangular cover 28 adjacent to the rear surface of rectangular cover 28. A left upper hinge barrel 31, comprising a convex spherical left surface, extends downward from the lower surface of cover 28 adjacent to the rear surface of cover 28. A right-hand helical worm gear sector 32 of the cone-drive type, the axis of which includes the centers of the spherical surfaces of right upper hinge barrel 29 and left upper hinge barrel 31, extends downward from the lower surface of cover 28. A nozzle cap 33, comprising a cylindrical inner surface centered about the axis of bottle cap 12, a cylindrical outer surface centered about the axis of bottle cap 12 and a flat circular plate at its upper end, perpendicular to this axis, extends upward from the upper surface of cover 28, its inner surface being contiguous with the hole in cover 28. A nozzle cap lip 34 protrudes radially inward from the inner surface of nozzle cap 33. A cylindrical window 35 passes through cover 28. A cap cover 36 is a single part molded of firm flexible plastic material and comprises cover 28, right upper hinge barrel 29, left upper hinge barrel 31, worm gear sector 32, nozzle cap 33, nozzle cap lip 34 and window 35.

Right lower hinge barrel 25, left lower hinge barrel 26, right upper hinge barrel 29 and left upper hinge barrel 31 have dimensions, finishes and locations such that their spherical concave and convex surfaces remain in tight contact, forming a hinge, allowing angular movement of cap cover 36 relative to sealing cap 27.

Sealing boss 18, sealing boss lip 19, nozzle cap 33 and nozzle cap lip 34 have dimensions, finishes and locations such that nozzle cap 33 may be snapped onto sealing boss 18 to effect a fluid-tight seal.

A cylindrical bottle 37 lies beneath a cylindrical bottle neck 38, which comprises a cylindrical inner surface and a cylindrical outer surface. A raised bottle neck lip 39 extends radially inward from inner surface of bottle neck 38. A single part molded of firm, flexible plastic material comprises bottle 37, bottle neck 38 and bottle neck lip 39.

Bottle cap 12, insertion ring 13, insertion ring lip 14, bottle neck 38 and bottle neck lip 39 have dimensions, finishes and locations such that insertion ring 13 may be snapped into bottle neck 38 to effect mechanical joining of the parts and a fluid-tight seal.

Ring 41 comprises a first planar surface, a second planar surface parallel to the first planar surface, a cylindrical outer surface, the axis of which is perpendicular to the first planar surface and a cylindrical hole centered about the axis of the outer surface. Radial ratchet tooth set 42 comprises thirteen radially sloping ratchet teeth and one cylindrical surface, together occupying fourteen equal angular spaces, these teeth projecting outward from the outer surface of ring 41. A symbol set 43 comprising fourteen symbols, the sequential Arabic numerals "1" through "13" followed by a star, is raised, arranged in a circular formation, upon the first planar surface of ring 41, these symbols occupying fourteen equal angular spaces. Axial ratchet tooth set 44 comprises fourteen axially sloping wedge-shaped ratchet teeth, these wedges lying base-to-apex in a circular formation, occupying fourteen equal angular spaces, projecting downward from the second planar surface of ring 41. Indicator ring 45 is a single part molded of firm flexible plastic material and comprises ring 41, radial ratchet tooth set 42, symbol set 43 and axial ratchet tooth set 44.

Sealing cap 27 and indicator ring 45 have dimensions, finishes and locations such that indicator ring 45 may be pressed onto bearing boss 15 and retained by set of retention lips 16 allowing a slip fit for relative rotation of these parts.

Axial ratchet tooth set 44 and backcheck pawl 17 have dimensions, finishes and locations such that indicator ring 45 is restricted from clockwise rotation, when viewed from above.

Worm gear sector 32, radial ratchet tooth set 42, backcheck pawl 17, axial ratchet tooth set 44, window 35 and symbol set 43 have dimensions, finishes and locations such that, when cover 28 is raised from the horizontal closed position to a position approximately vertical and subsequently returned to the closed position, worm gear sector 32 first will slide over the surface of the juxtaposed tooth of radial ratchet tooth set 42, indicator ring 45 being restricted from reverse rotation, and fall into the following space, then drive indicator ring 45 one fourteenth of a revolution, bringing the next symbol of symbol set 43 into view through window 35. If cylindrical space of radial ratchet tooth set 42, rather than a tooth of radial ratchet tooth set 42 is swept by worm gear sector 32, indicator ring 45 does not rotate and the star symbol of symbol set 43 remains in position under window 35.

FIG. 1B depicts the underside of indicator ring 45 of the preferred embodiment of the invention, for further clarity.

OPERATION OF THE PREFERRED EMBODIMENT

The present invention in its preferred embodiment may be used in the care of disposable soft contact lenses, which are typically prescribed for fourteen days of waking-hours-only wear with nightly removal, cleaning and storage. A contact lens wearing cycle ends when the wearer removes the contact lenses in the evening and observes the star symbol of symbol set 43 in window 35, prior to lifting cap cover 36 from sealing cap 27. Rather than executing the regular nightly cleaning and storage procedure, this serves as the wearer's cue to discard the old lenses.

The next morning contact lenses are to be worn, the wearer commences using a fresh pair of lenses and manually rotates indicator ring 45 until it clicks, without lifting rectangular cover 28. The "1" symbol of symbol set 43 at this point is visible through window 35. Thereby the next cycle commences. On the evening of the first day of this new cycle, the wearer observes the "1" of symbol set 43 through window 35 prior to lifting cap cover 36 from sealing cap 27, lifts cap cover 36 from sealing cap 27, uses the enclosed contact lens care solution in accordance with the prescribed care regimen, then presses cap cover 36 down onto sealing cap 27, thereby automatically indexing indicator ring 45 by one position. This continues until, on the evening of the thirteenth day, the wearer observes the "13" of symbol set 43, then on the evening of the fourteenth day the wearer observes the star symbol of symbol set 43, which serves as a cue to abstain from lifting cap cover 36 from sealing cap 27, to discard the used contact lenses, thereby ending this cycle, the next morning to commence the use of a new pair of lenses and then to manually index indicator ring 45 by one position.

DESCRIPTION OF THE FIRST ALTERNATE EMBODIMENT

FIG. 2

Figure 2:
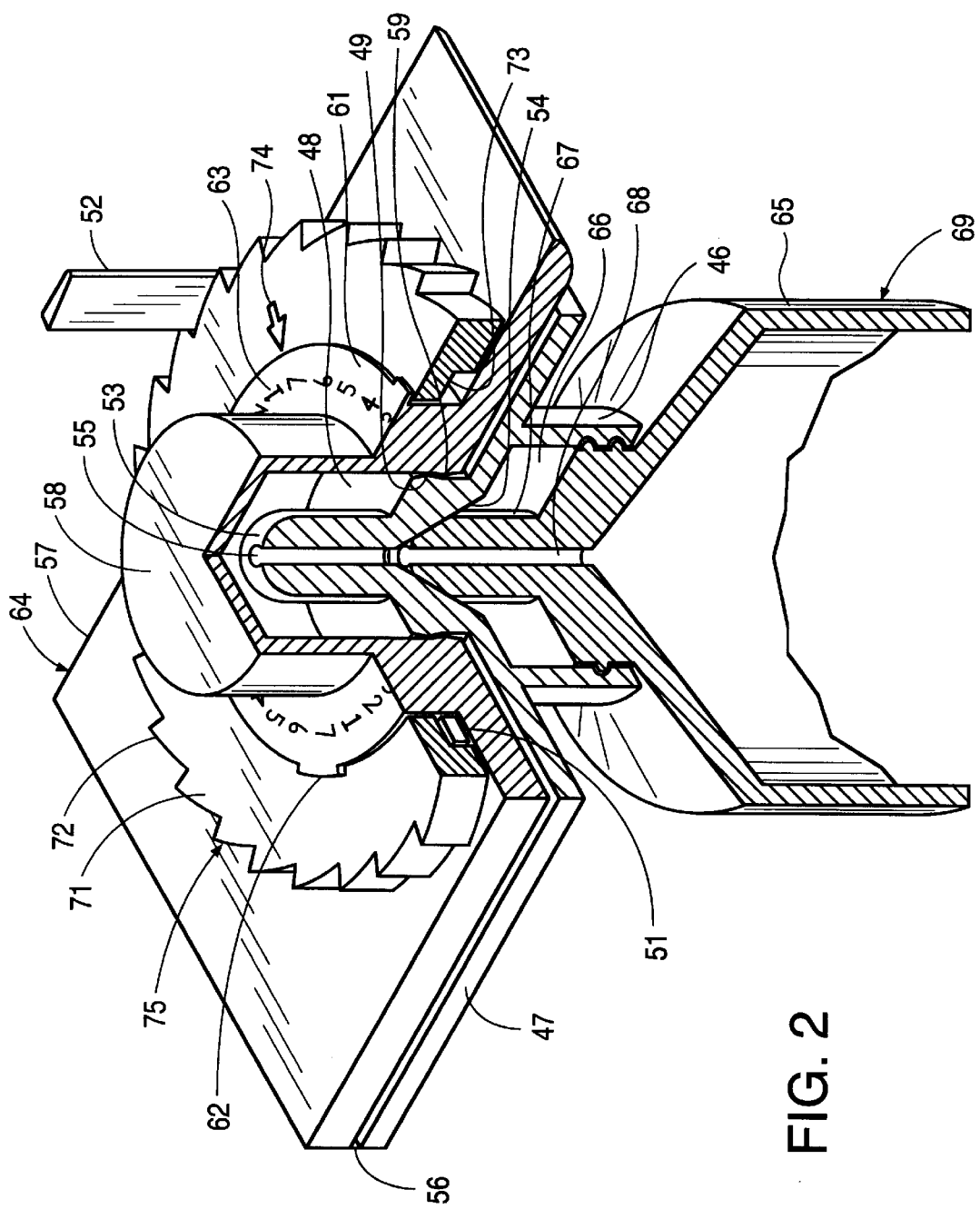
FIG. 2 depicts a first alternate embodiment of the present invention, in which the counting mechanism is integrated into a screw-on cap, nozzle and nozzle cap assembly, which is mounted upon and sealed onto a bottle, which bears its own screw thread and nozzle, assembled, in the closed condition, in perspective view, sectioned to illustrate detail.

FIG. 2 is an assembly view with break-away sections illustrating a first alternate embodiment of the invention. A hollow cylindrical threaded tube 46 comprises an inner cylindrical surface bearing a right-hand female screw thread, centered about an axis and an outer cylindrical surface centered about the axis of the inner cylindrical surface. A rectangular base plate 47, comprising a lower surface, an upper surface, a right surface and a rear surface, lies atop threaded tube 46. A sealing protuberance 48, comprising an outer cylindrical surface centered about the axis of threaded tube 46 and a flat upper surface, projects upward from base plate 47. A raised sealing protuberance edge 49 protrudes radially outward from the outer surface of sealing protuberance 48. A wedge-shaped reversal prevention pawl 51 projects upward from the upper surface of base plate 47 adjacent to the outer surface of sealing protuberance 48, sloping upward in the direction of counter-clockwise rotation about the axis of threaded tube 46. A long, bar-shaped drive pawl 52, trapezoidal in cross section, narrow in radial dimension to allow sideward elastic deflection, extends upward from the upper surface of base plate 47, adjacent to the right surface of base plate 47. A cylindrical spout 53, centered about the axis of threaded tube 46, projects upward from upper surface of sealing protuberance 48. An upward pointing conical sealing cavity 54 intrudes into lower surface of base plate 47, centered about the axis of threaded tube 46. A narrow communicating hole 55, centered about the axis of threaded tube 46, connects the space within sealing cavity 54 and threaded tube 46 with the space above spout 53. A thin living hinge 56, comprising a lower edge and an upper edge, extends upward from base plate 47 at the junction of the upper surface of and the rear surface of base plate 47. A flat rectangular cover plate 57, comprising a lower surface, an upper surface, a right surface, a rear surface and a cylindrical hole, centered about the axis of threaded tube 46, is contiguous with the upper edge of living hinge 56 at the junction of the lower surface of and the rear surface of cover plate 57, and is clear of drive pawl 52 on its right side, all orientations being judged with cover plate 57 folded down into close juxtaposition with the upper surface of base plate 47. A cylindrical spout cap 58, comprising an inner cylindrical surface, centered about the axis of threaded tube 46, an outer cylindrical surface centered about the axis of threaded tube 46, and an upper plate, perpendicular to this axis, extends upward from the upper surface of cover plate 57, its inner surface being contiguous with the hole in cover plate 57, is open at its lower end. A raised spout cap edge 59 protrudes radially inward from the inner surface of spout cap 58. A cylindrical bearing protuberance 61, comprising an outer cylindrical surface, centered about the axis of threaded tube 46, and an upper surface, perpendicular to this axis, projects upward from the upper surface of cover plate 57 and radially outward from the outer surface of spout cap 58. An equally spaced set of keeper lips 62, three in number, protrudes radially outward from the outer surface of bearing protuberance 61 adjacent to the upper surface of bearing protuberance 61. A character set 63 comprising twenty-eight symbols, four iterations of the sequential Arabic numerals "1" through "7", is raised, arranged in a circular formation, upon the upper surface of bearing protuberance 61. Sealing top 64 is a single part molded of firm flexible plastic material and comprises threaded tube 46, base plate 47, sealing protuberance 48, sealing protuberance edge 49, reversal prevention pawl 51, drive pawl 52, spout 53, sealing cavity 54, communicating hole 55, living hinge 56, cover plate 57, spout cap 58, spout cap edge 59, bearing protuberance 61, set of keeper lips 62 and character set 63.

Sealing protuberance 48, sealing protuberance edge 49, spout cap 58 and spout cap edge 59 have dimensions, finishes and locations such that spout cap 58 may be snapped onto sealing protuberance 48 to effect mechanical retention and a fluid-tight seal.

A cylindrical vessel body 65 lies beneath a cylindrical vessel neck 66, which comprises a cylindrical outer surface, bearing a right-hand male screw thread and an axis. A cylindrical vessel nozzle 67, centered about the axis of vessel neck 66 projects upward from the upper surface of vessel neck 66. A cylindrical transmission hole 68, centered about the axis of vessel neck 66, connects the cavity within vessel body 65 with the space above vessel nozzle 57. Vessel 69 is a single part molded of first flexible plastic material and comprises vessel body 65, vessel neck 66, vessel nozzle 67 and transmission hole 68.

Threaded tube 46, base plate 47, sealing cavity 54, vessel neck 66 and vessel nozzle 67 have dimensions, finishes and locations such that sealing top 64 may be screwed onto vessel 69 for mechanical retention and to effect a fluid-tight seal.

A wheel 71 comprises a first planar surface, a second planar surface parallel to the first planar surface, an outer cylindrical surface centered about an axis perpendicular to the first planar surface and a cylindrical hole, centered about the axis of the outer surface. Outer ratchet tooth set 72 comprises twenty-eight equally spaced radially sloping ratchet teeth, these teeth projecting outward from the outer surface of wheel 71. Lower ratchet tooth set 73 comprises twenty-eight axially sloping wedge-shaped ratchet teeth, these teeth lying base-to-apex in a circular formation, occupying twenty-eight equal angular spaces, projecting downward from the second planar surface of wheel 71. On the upper surface of wheel 71 is a raised indicator arrow 74, pointing toward the axis of wheel 71. Indicator wheel 75 is a single part molded of firm flexible plastic material and comprises wheel 71, outer ratchet tooth set 72, lower ratchet tooth set 73 and indicator arrow 74.

Sealing top 64 and indicator wheel 75 have dimensions, finishes and locations such that indicator wheel 75 may be pressed onto bearing protuberance 61 and retained by set of keeper lips 62 allowing a slip fit for relative rotation of these parts.

Lower ratchet tooth set 73 and reversal prevention pawl 51 have dimensions, finishes and locations such that indicator wheel 75 is restricted from clockwise rotation, when viewed from above.

Reversal prevention pawl 51, drive pawl 52, character set 63, outer ratchet tooth set 72, lower ratchet tooth set 73 and indicator arrow 74 have dimensions, finishes and locations such that, when cover plate 57 is raised from the horizontal closed position to a position approximately vertical and subsequently returned to the closed position, first, drive pawl 52 bends to slide over the juxtaposed tooth of outer ratchet tooth set 72, indicator wheel 75 being restricted from reverse rotation, and falls into the following space, then drives indicator wheel 75 one twenty-eighth of a revolution, bringing indicator arrow 74 into alignment with the next numeral of character set 63.

OPERATION OF THE FIRST ALTERNATE EMBODIMENT

The present invention in its first alternate embodiment may be used, among other ways, in the care of contact lenses, often prescribed for waking-hours-only wear with nightly removal, cleaning and storage, with an additional enzyme cleaning every seventh day. The contact lens storage solution bottle is opened nightly, each opening indexing indicator wheel 75 by one tooth of outer ratchet tooth set 72. When, in preparing to perform the nightly cleaning, the user sees that the arrow is aligned with a character "7" of character set 63 prior to lifting cover plate 57, the wearer is thereby prompted to perform the additional enzyme cleaning procedure. On the following night, a character "1" of character set 63 is observed prior to lifting cover plate 57, and so on, until a character "7" of character set 63 is again indicated prior to lifting cover plate 57, thereby instigating the next enzyme cleaning.

DESCRIPTION OF THE SECOND ALTERNATE EMBODIMENT

Figure 3A:
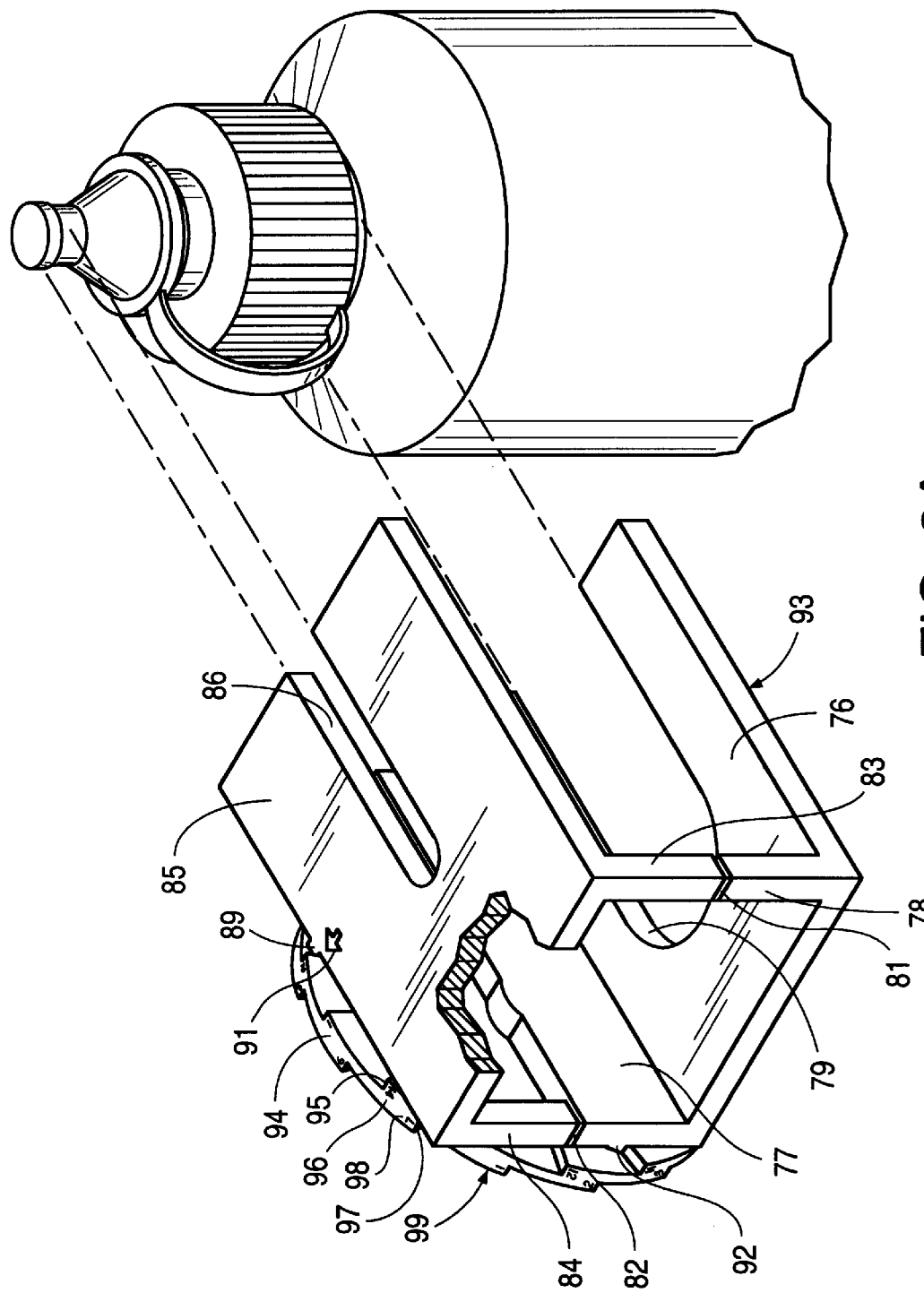
FIG. 3A depicts a second alternate embodiment of the present invention, in which the counting mechanism is integrated into a device which can be clipped onto a separate bottle, cap, nozzle and nozzle cap assembly, this assembly being shown as well, for clarity, assembled, in the closed condition, in perspective view, sectioned to illustrate detail.
Figure 3B:
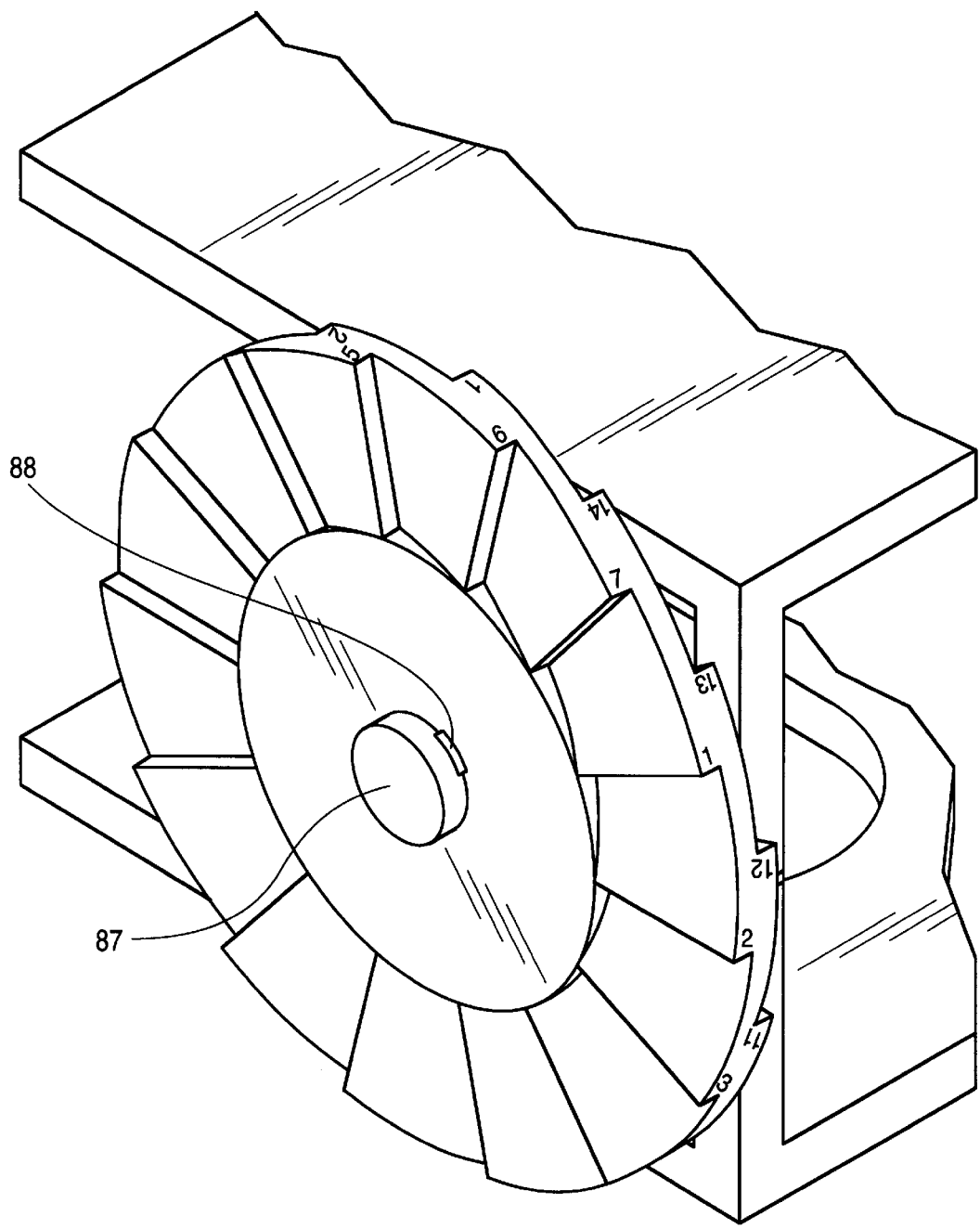
FIG. 3B depicts the rotary mechanism of the second alternate embodiment of the invention from an alternate perspective, for further clarity.

FIGS. 3A and 3B

FIG. 3A is an assembly view with break-away sections illustrating a second alternate embodiment of the invention. Also shown in FIG. 3A is a bottle apparatus of a familiar type, standard in the eye contact lens solution industry, comprising a container, a neck, an expulsion member and an expulsion member cap, to which the invention can be attached for operation.

A rectangular lower gripping plate 76, comprising a left surface, a right surface, an upper surface, a front surface and a rear surface is oriented horizontally. A rectangular support wall 77, comprising a rear surface and an upper surface, protrudes upward from the upper surface of lower gripping plate 76 adjacent to the right surface of lower gripping plate 76. A left lower leg 78, comprising a rear surface and an upper surface, extends upward from upper surface of lower gripping plate 76 adjacent to the junction of rear surface of and left surface of lower gripping plate 76. A lower slot 79 lies in lower gripping plate 76, open at the front surface of lower gripping plate 76 and extending rearward, ending in a semicircular surface. A left integral hinge 31, comprising a lower edge and an upper edge, projects upward prom the junction of the rear surface of and the upper surface of left lower leg 78. A right integral hinge 82 projects upward from the junction of the rear surface of and the upper surface of support wall 77. A left upper leg 83, comprising a rear surface, an upper surface and a lower surface, projects upward from the upper edge of left integral hinge 81 at the junction of the rear surface of and the lower surface of left upper leg 83. A right upper leg 84, comprising a rear surface, a lower surface and an upper surface, projects upward from upper edge of right integral hinge 82 at the junction of the rear surface of and the lower surface of right upper leg 84. A horizontal rectangular upper gripping plate 85 projects forward from the upper surface of left upper leg 83 and upper surface of right upper leg 84, upper gripping plate 85 being parallel to lower gripping plate 76, all directions being judged with lower gripping plate 76 and upper gripping plate 85 lying parallel. An upper slot 86 lies in upper gripping plate 85, open at the front surface of upper gripping plate 85 and extending rearward, ending in a semicircular surface, the semicircular surface of upper slot 86 being coaxial With the semicircular surface of lower slot 79. A cylindrical side-mounted journal 87, this particular feature being indicated on FIG. 3B, projects horizontally outward from the right surface of support wall 77, adjacent to the upper surface of support wall 77, having its axis horizontal, comprising a distal end. A raised set of holding lips 88, two in number, projects radially outward from the distal end of side-mounted journal 87. A trapezoidal thrust pawl 89 extends rightward from the right surface of upper gripping plate 85. A pointer arrow 91 is raised on the upper surface of upper gripping plate 85, pointing toward the edge of upper gripping plate 85 near thrust pawl 89. A trapezoidal antireversion pawl 92 projects horizontally rightward from the right surface of support wall 77, adjacent to the rear surface of support wall 77. Gripping unit 93 is a single part molded of firm flexible plastic material and comprises lower gripping plate 76, support wall 77, left lower leg 78, lower slot 79, left integral hinge 81, right integral hinge 82, left upper leg 83, right upper leg 84, upper gripping plate 85, upper slot 86, side mounted journal 87, set of holding lips 88, thrust pawl 89, pointer arrow 91 and antireversion pawl 92.

Lower gripping plate 76, lower slot 79, upper gripping plate 85, and upper slot 86 have dimensions, finishes and locations such that, simultaneously, lower slot 79 can be manually forced onto the neck of the container and upper slot 86 can be manually forced onto the cylindrical surface of least diameter of the expulsion member cap, with interference for retention, while the expulsion member cap is in the snapped-on position, and such that left integral hinge 81 and right integral hinge 82 allow the expulsion member cap to snap off of and swing clear of the expulsion member with the exertion of upward manual force on upper gripping plate 85.

Disc 94 comprises a first planar surface, a second planar surface parallel to the first planar surface, an axis perpendicular to the first planar surface, a circumferential outer surface centered about this axis and a cylindrical hole, centered about this axis. A first ratchet tooth set 95 comprises fourteen contiguous, equally spaced, axial ratchet teeth, each tooth protruding from the first planar surface of disc 94, in a direction parallel to the axis of the cylindrical hole of disc 94. A first numeral set 96 comprising the fourteen equally spaced, sequential Arabic numerals "1" through "14" is raised, arranged along the circumferential surface of disc 94, each numeral being adjacent to one tooth of first ratchet tooth set 95 and having its left side closest to the adjacent tooth of first ratchet tooth set 95. A second ratchet tooth set 97 comprises fourteen contiguous, equally spaced, axial ratchet teeth, each tooth protruding from the second planar surface of disc 94 in a direction parallel to the axis of the cylindrical hole of disc 94. A second numeral set 98 comprising the fourteen equally spaced, sequential Arabic numerals "1" through "7", then "1" through "7" is raised, arranged along the circumfrencial surface of disc 94, each numeral being adjacent to one tooth of second ratchet tooth set 97 and having its left side closest to the adjacent tooth of second ratchet tooth set 97. An indicator disc 99 is a single part molded of firm flexible plastic material and comprises disc 94, first ratchet tooth set 95, first numeral set 96, second ratchet tooth set 97 and second numeral set 98.

Gripping unit 93 and indicator disc 99 have dimensions, finishes and locations such that indicator disc 99 may be pressed onto side-mounted journal 87 and retained by set of holding lips 88, allowing a slip fit for relative rotation of these parts. Indicator disc 99 may be manually removed, flipped over and reinstalled on side-mounted journal 87.

First ratchet tooth set 95, second ratchet tooth set 97 and antireversion pawl 92 have dimensions, finishes and locations such that indicator disc 99 is restricted from reverse rotation.

Thrust pawl 89, pointer arrow 91, antireversion pawl 92, first ratchet tooth set 95, first numeral set 96, second ratchet tooth set 97, and second numeral set 98 have dimensions, finishes and locations such that, when upper gripping plate 85 is raised from the horizontal, closed position to a position approximately vertical, thrust pawl 89 first rotates indicator disc 99, causing the juxtaposed tooth of first ratchet tooth set 95 or second ratchet tooth set 97 to slide over antireversion pawl 92, allowing antireversion pawl 92 to fall into the following space, side-mounted journal 87 being flexible to allow adequate deflection of indicator disc 99, thrust pawl 89 abandoning indicator disc 99 immediately thereafter. When upper gripping plate 85 is manually pressed back down into a position parallel to lower gripping plate 76, a position maintained by snapping the expulsion member cap onto the expulsion member, thrust pawl 89 slides over the juxtaposed tooth of first ratchet tooth set 95 or second ratchet tooth set 97 and falls into the following space, reverse rotation being prohibited by the relative positions of antireversion pawl 92 and first ratchet tooth set 95 or second ratchet tooth set 97. Upon completion of this procedure, one fourteenth of a rotation has occurred and pointer arrow 91 points toward the next sequential element of first numeral set 96 or second numeral set 98.

OPERATION OF THE SECOND ALTERNATE EMBODIMENT

The present invention in its second alternate embodiment may be used, among other ways, in displaying a transient record of instillation of therapeutic eye drops, used once per day, thereby reducing the user's dependence upon memory and allowing automatic confirmation of accurate dosing over the course of either one week or two weeks, depending upon which way indicator disc 99 is flipped. Resetting the position of indicator disc 99 may be executed by repeated opening and closure of the assembly or by manual rotation of indicator disc 99.

The present invention in its second alternate embodiment may also be used, among other ways, in the care of contact lenses, often prescribed for waking-hours-only wear with nightly removal, cleaning and storage, with an additional enzyme cleaning every seventh day. The contact lens storage solution bottle apparatus is opened and closed once per night, each opening indexing indicator disc 99 by one tooth of second ratchet tooth set 97. When, in preparing to perform the nightly cleaning, the wearer sees that the arrow is aligned with one of the characters "7" of second numeral set 98 prior to removing the nozzle cap, with indicator disc flipped so that second radial ratchet tooth set 97 faces thrust pawl 89, the wearer is thereby prompted to perform the additional enzyme cleaning procedure. On the following night a character "1" of second numeral set 98 is observed, prior to removing the nozzle cap, and so on, until the second character "7" of second numeral set 98 is indicated, prior to removing the nozzle cap, thereby instigating the next enzyme cleaning.

CONCLUSION, RAMIFICATIONS AND SCOPE OF THE INVENTION

The automatic squeeze-bottle utilization cycle counting device provides a convenient, simple-to-use and reliable method of keeping track of the number of times a squeeze-bottle containing a liquid, such as a liquid pharmaceutical agent or contact lens solution, has been either opened or closed in a given time period, or as a running total, or by association, the number of times another activity has been performed. This is a function heretofore accomplished by memory, calendars and paper records, often resulting in inadvertent significant noncompliance with prescribed regimens. The parts of the described embodiments of the invention are simple and can be produced and assembled economically. The invention allows for improved hygiene by decreasing the risk of digital contamination of the nozzle tip and thereby of the contents. It serves to facilitate removal of the nozzle cap, providing greater assurance that the nozzle cap will be used in the manner intended, so as to further decrease the risk of contamination.

While the above description contains many specificities, these should not be construed as limitations on the scope of the invention, but rather as exemplifications of some practical embodiments thereof. Many other variations are possible, for example, the set of symbols could be replaced with a spiral line, various words, icons and colors could be used to alert the user to the condition of the mechanism, the simple hinges could be replaced with spring-back hinges which provide angular location in an open position, various other mechanisms could be utilized for the purpose of rotating the wheel, the wheel could be replaced with a rotatable object of a different shape, such as a triangle or a pointer, a secondary mechanism could be incorporated so as to flag the user that a wheel cycle has been completed, the device could bear surfaces for the display of advertising information, means to prevent reapplication of the nozzle cap to the nozzle at the end of a wheel cycle in the absence of manual intervention could be incorporated, the bottle could have any of a variety of shapes, the bottle and the cap could be molded as a single part and the hinge could incorporate an angular location leaf, for holding the upper part of the unit in the open position during use. Accordingly, the scope of the invention should be determined not by the embodiments illustrated, but by the appended claims and their legal equivalents.

I claim as new the following:

1. A resealable liquid containment and dispensing apparatus, for the automatic recording of the number of serial dispensings of liquid, performed or yet to be performed, in a given cycle, comprising:

a necked, manually deformable bottle;

a bottle cap member, attached and sealed to said bottle;

a nozzle formed on said bottle cap member and a hole passing through said nozzle and said bottle cap member;

a nozzle cap removably sealable onto said nozzle, providing, while said nozzle cap is sealed onto said nozzle, the isolation of said nozzle and said liquid contents from the outside environment, and allowing, when said nozzle cap is removed from said nozzle, the controlled expulsion of said liquid contents through said nozzle by the generation of positive internal fluid pressure, through manual deformation of said bottle;

a rotatable ring member, mounted upon said bottle cap member;

a radial ratchet tooth set, projecting from said ring, said ratchet teeth positioned on equal angular spaces, the number of said spaces being at least equal to the number of said ratchet teeth present;

forward indexing means attached to said nozzle cap, said indexing means resting in a notch at the juncture of two of said ratchet teeth while said nozzle cap is sealed onto said nozzle, said indexing means communicating with a radial surface of one of said teeth, rotating said ring member through an angle equal to the angle occupied by one of said ratchet teeth, during a removal and resealing cycle of said nozzle cap;

means to prevent rotation of said ring member on said ring member and said bottle cap member, comprising a backcheck pawl on one of said members and a second ratchet tooth set on the other of said members;

indicating means on said ring member and said nozzle cap for recording the number of dispensings of liquid; comprising equally spaced sequential symbols on one of said ring member and said nozzle cap and means for sequential indication of said symbols on the other of said ring member and said nozzle cap.

\* \* \* \* \*